United States Patent [19]

Pieniak

[11] 4,010,754
[45] Mar. 8, 1977

[54] TAB FASTENER HAVING SUBSTANTIALLY COPLANAR DIVERGING ANCHORING LEGS

[75] Inventor: Heinz A. Pieniak, Chicago, Ill.

[73] Assignee: Johnson & Johnson, New Brunswick, N.J.

[22] Filed: Feb. 4, 1976

[21] Appl. No.: 655,047

[52] U.S. Cl. .......................... 128/287; 24/DIG. 11
[51] Int. Cl.² ........................................ A41B 13/02
[58] Field of Search .......... 128/287, 284, 286, 288, 128/290, 290 H, 156; 24/DIG. 11, 67 AR

[56] References Cited
UNITED STATES PATENTS

| | | | |
|---|---|---|---|
| 2,846,134 | 8/1958 | Moubayed | 24/DIG. 11 |
| 3,724,033 | 4/1973 | Baker | 24/67 AR |
| 3,967,622 | 7/1976 | Cepuritis | 128/287 |

Primary Examiner—Stephen C. Pellegrino

[57] ABSTRACT

A disposable diaper having a facing sheet defining a diaper inside surface for direction toward an infant and a backing sheet defining a diaper outside surface is provided with adhesive tabs having a fixed end and a free end. The fixed end has an adhesive coating on one face thereof for permanently attaching the fixed end of the tab to a marginal portion of the diaper outside surface. The fixed end is divided lengthwise to define anchoring legs which are contiguous at a location spaced inwardly from the terminal edge of the fixed end and are diverging with respect to one another to a spaced-apart position at the terminal edge of the fixed end for facilitating in distributing stresses imposed on the tape segment. The free end has an adhesive coating on one face thereof, and release means is releasably attached to the adhesive coating on the free end of the tab. The free end is separable from the release means to make the free end available for use in securing the diaper about an infant.

12 Claims, 6 Drawing Figures

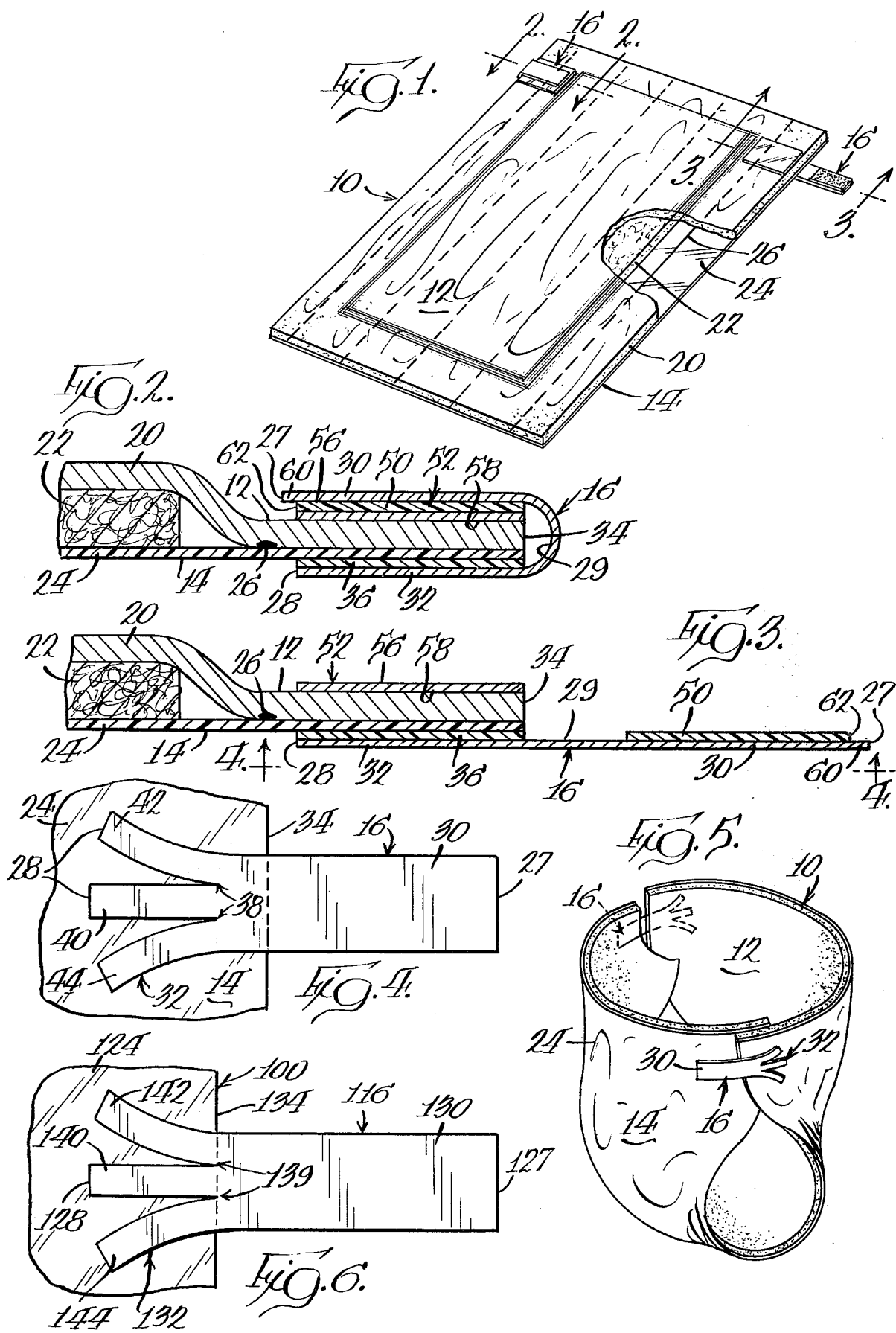

TAB FASTENER HAVING SUBSTANTIALLY COPLANAR DIVERGING ANCHORING LEGS

BACKGROUND OF THE INVENTION

This invention relates to disposable diapers. More particularly, this invention relates to disposable diapers adapted to be secured in place by adhesive tabs.

Disposable diapers provide substantial advantages in convenience over diapers intended to be laundered and reused particularly when they are used away from home. In recent years, many different disposable diapers have beep proposed and some have been successful in the marketplace. Typical disposable diaper structures comprise a moisture-retaining layer of high liquid-holding capacity and a moisture-impervious backing sheet therefor, generally made of a plastic film such as polyethylene film or the like. Typical disposable diaper structures are shown in U.S. Pat. No. 3,612,055 to Mesek et al. and in U.S. Pat. No. Re. 26,151 to Duncan et al.

As may be seen from the above-cited patents, it is desirable to obviate the problems that are inherent in closure systems which utilize extraneous fasteners such as safety pins, snaps and zippers. To this end adhesive closure systems have presented acceptable solutions.

Prior art adhesive closure systems disclose tab fasteners having one end permanently attached to a relatively strong backing sheet on the diaper and an opposite end available for securement to an adjacent corner of the diaper. The stresses imposed on the tab fastener are transferred to the portion of the backing sheet to which the tab fastener is secured. The concentrated application of such stresses to a small segment of the backing sheet has the disadvantage that undesirable rupture of the diaper backing sheet can result.

SUMMARY OF THE INVENTION

According to the present invention, tape tabs are used on each side of a diaper to secure the diaper about an infant. Each tab has a free end which extends longitudinally to one transverse edge of the tab and a fixed end which extends longitudinally in a direction opposite from the free end to the opposite transverse edge of the tab. The fixed end has an adhesive coating on one face thereof for permanently attaching the tab to a marginal portion of the backing sheet, and at least two substantially coplanar anchoring legs which are contiguous at a location between the transverse edges and which diverge with respect to one another to a spaced-apart position at the transverse edge of the fixed end so as to facilitate distribution of stresses imposed on the tab. The free end has a pressure-sensitive adhesive coating on one face thereof, and release means is releasably attached to the adhesive-coated free end so as to protect the adhesive coating thereon prior to use. The free end is separable from the release means to make the adhesive-coated free end available for use in securing the diaper about an infant.

The release means may comprise a release coating printed or otherwise deposited on a portion of the diaper inside surface, a release strip having a release coating on one face thereof and an adhesive coating on the opposite face by means of which the release strip is adhered to the diaper, or other suitable means for releasably adhering the free end of the tab to the diaper. Gripping means may also be provided on the tab to facilitate separation of the free end of the tab fron the release means preparatory to fastening the diaper about an infant.

By attaching the diverging anchoring legs to the backing sheet, stresses imposed on the backing sheet as the infant moves about are more widely distributed through the diaper to minimize the possibility of undesirable rupture of the backing

BRIEF DESCRIPTION OF THE DRAWINGS

FIG. 1 is a perspective view, partially broken away to show interior detail, of an open unfolded diaper in accordance with the present invention;

FIG. 2 is an enlarged fragmentary cross-sectional view of the diaper of FIG. 1 taken along plane 2—2;

FIG. 3 is an enlarged fragmentary cross-sectional view of the diaper of FIG. 1 taken along plane 3—3;

FIG. 4 is a fragmentary plan view on a smaller scale taken along plane 4—4 in FIG.3;

FIG. 5 is a perspective view of the diaper of FIG. 1 in a configuration assumed by the diaper when placed about an infant; and FIG. 6 is a fragmentary plan view similar to FIG. 4 and showing an alternate embodiment of the invention.

DESCRIPTION OF THE PREFERRED EMBODIMENTS

In the following description, two digit numerals are used to refer to the embodiment illustrated in FIGS. 1–5 and three digit numerals in the one hundred series are used to refer to the embodiment illustrated in FIG. 6. The same last two digits in each numeral designate similar elements in the various embodiments.

Disposable diaper 10, illustrated in FIGS. 1 and 5, is of substantially quadrilateral configuration and presents inside surface 12 for direction toward an infant and outside surface 14 for direction away from the infant. Adhesive tab fastener means comprising tape segments such as tabs 16 are attached to diaper 10 for securing diaper 19 about an infant. As described in greater detail below, tabs 16 are movable from a folded-over storage position illustrated in FIG. 2 to a working position which is illustrated in FIG. 3.

Referring to FIGS. 1–3, diaper 10 comprises moisture-impervious facing sheet 20, defining diaper inside surface 12 and overlying moisture-retaining absorbent pad 22, and backing sheet 24 which is made of a moisture-impervious material and defines diaper outside surface 14. Absorbent pad 22 is somewhat smaller than backing sheet 24 and is centrally disposed thereon; however, absorbent pad 22 can be made coextensive with backing sheet 24, if desired. Facing sheet 20 is substantially coextensive with backing sheet 24. Both facing sheet 20 and pad 22 can be anchored to the backing sheet 24 by means of adhesive beads 26, glue spots or in any other convenient manner. For example, facing sheet 20 and pad 22 can be secured together by heat bonding.

As illustrated in FIGS. 2 and 3, adhesive tab 16 has terminal edges 27 and 28, inner face 29, free working end 30 which extends to outer transverse edge 27, and fixed end 32 which extends from free end 30 to inner transverse edge 28. Free end 30 is adapted to be folded about longitudinal edge 34 of diaper 10 so as to assume the folded-over storage position of FIG. 2.

Fixed end 32 is provided with adhesive coating 36 on inner face 29 thereof for permanently attaching fixed end 32 of tab 16 to backing sheet 24 at a marginal location on the backing sheet. Adhesive coating 36 can be a pressure-sensitive adhesive composition, a heat-activated or solvent-activated composition, or the like. Fixed end 32 is divided or digitated lengthwise to define a plurality, in this particular instance three, substantially coplanar anchoring legs which are contiguous at locations 38 spaced from inner transverse edge 28 and which diverge with respect to one another to a spaced-apart position at transverse edge 28 of fixed end 32 to facilitate distribution of stresses imposed on tab 16. In other instances the number of coplanar legs can be more or less as desired. From the standpoint of manufacturing expedience on a high-speed production line, it is preferable to provide a fixed end having two coplanar legs. The diverging anchoring legs have the capacity to absorb and distribute stresses imposed on tab 16 as the infant moves about to thereby minimize the load imposed on free end 30 of the tab. By distributing the stresses to backing sheet 24, the diverging anchoring legs minimize the possibility of undesirable rupture of backing sheet 24.

In the embodiment illustrated in FIG. 4, fixed end 32 includes a middle anchoring leg 40 and a pair of coplanar anchoring legs 42, 44 flanking middle leg 40. Flanking legs 42, 44 diverge from middle leg 40 in opposite directions.

Free end 30 and fixed end 32 preferably are about equal in length. In the embodiment illustrated in FIG. 4, anchoring legs 40, 42, 44 extend from transverse edge 28 of fixed end 32 to locations 38 intermediate transverse edges 27, 28 and which locations are spaced inwardly from longitudinal margin or edge 34 of diaper 10. Alternatively, as illustrated in FIG. 6, anchoring legs 140, 142, 144 of tab 116 may extend from transverse edge 128 of fixed end 132 to locations 139 situated intermediate transverse edges 127, 128. Locations 139 are adjacent to longitudinal margin 134 of diaper 100. Similarly to tab 16, tab 116 has fixed end 132 and free end 130.

Pressure-sensitive adhesive coating 50 is provided on inner face 29 of free end 30, faces in the same direction as diaper inside surface 12 when tab 16 is in the working position, and provides a securement means which can be moved from a closed, storage position shown in FIG. 2 to an open working position of FIG. 3 preparatory to fastening the diaper about an infant. If desired, adhesive coating 36 on fixed end 32 may be a pressure-sensitive adhesive coating and the adhesive coatings on free end 30 and fixed end 32 may comprise a substantially continuous adhesive coating on inner face 29 of tab 16.

Release means 52 is carried by diaper 10 at a marginal location thereon and provides a release region facing substantially in the same direction as diaper inside surface 12. The release means is at least as wide as adhesive coating 50 on free end 30 of tab 16. When tab 16 is in the storage position of FIG. 2 adhesive coating 50 is releasably adhered to release means 52 which is substantially coextensive with adhesive coating 50.

Release means 52 may comprise a ribbon segment or release strip carried by diaper 10 and provided with a release coated face 56 which provides the release region and faces in the same direction as diaper inside surface 12, and an adhesive coating on opposite face 58 by means of which the release strip is anchored to diaper inside surface 12. Release coated face 56 faces in the same direction as diaper inside surface 12 along first anchoring leg 30. Alternatively, release means 52 may comprise a release coating, such as a silicone release compound, or the like, on a marginal portion of diaper inside surface 12 and which is substantially coextensive with adhesive coating 50 on free end 30 when tab 16 is folded to the storage position.

It is desirable to provide a gripping means to facilitate grasping tab 16 for separating adhesive coating 50 on free end 30 of tab 16 from release means 52 preparatory to fastening the diaper about an infant. As shown in FIGS. 2 and 3, free end 30 can include projecting portion 60 which extends inwardly on diaper 10 beyond outermost edge 62 of adhesive coating 50. The outwardly extending segment 60 provides a convenient gripping means for separating adhesive coating 50 on free end 30 from release means 52.

Adhesive tabs suitable for the purposes of the present invention can be made from a wide variety of materials, provided that such materials are sufficiently flexible. Preferred materials for this purpose are polyalkylene webs such as polyethylene sheet, polypropylene sheet, and the like. Particularly preferred are webs which are oriented along the narrow dimension of the tab or webs which have filament reinforcements therein and elastic webs which further minimize the stresses transmitted to the diaper backing sheet.

The pressure-sensitive adhesive layers such as adhesive coating 50 are provided by applying a coating of a pressure-sensitive composition known in the art to the appropriate surface of tab 16. The applied adhesive shall have good tack, good cohesive strength, good resistance to moisture and good resistance to aging. Illustrative of such adhesive compositions are mixtures of natural or synthetic rubber, zinc oxide, and various resins, also latices of natural or synthetic rubber, or water dispersions of acrylic tacky polymers or copolymers, and the like.

Anchored release strips can be made from smooth plastic film having a relative non-adhering surface, from paper coated with a silicone release compound, or from similar release materials. A number of appropriate release coatings may be used with the present invention. Examples of such coatings, are disclosed in U.S. Pat. No. 2,822,290 to Webber; U.S. Pat. No. 2,880,862 to Sermattei; and U.S. Pat. No. 2,985,554 to Dickard.

Several different types of facing materials may be used for diaper facing sheet 20. For example, facing sheet 20 may be made up of a mixture of fibers consisting predominantly of inexpensive short cellulosic fibers such as wood pulp fibers or cotton linters, in amounts of about 75% to about 98%, the balance being textile length fibers such as rayon as described in U.S. Pat. No. 3,663,348 to Liloia et al.

Facing sheet materials suitable for use in this invention can have fabric weights in the range of about 1 to 5 oz./yd.$^2$ and densities of less than 0.15 g./cc., generally in the range between 0.05 and 0.1 g./cc. The dry strength of the facing sheet for a fabric having a weight of about 1.5 oz./yd.$^2$ is at least 0.15 lbs./in. of width in the machine direction and at least 0.1 lbs./in. of width in the cross direction. Such fabrics have unusually good elongation, loft, softness, and drape characteristics in comparison to prior products incorporating any substantial amount of short fibers.

Facing sheet 20 may also be made of an apertured, nonwoven fabric which is formed, for example, in accordance with the teachings of commonly assigned U.S. Pat. Nos. 2,862,251, 3,081,514 and 3,081,515.

Briefly, such fabrics are foraminous structures wherein groups or groupings of fibers have been rearranged from a fibrous nonwoven starting web into positions surrounding less dense fabric portions by passage of a fluid through the starting material. The fibers within the material. The fibers within the groupings are mechanically interlocked, and may be arranged into various patterns, as is well known by those skilled in the art. A suitable binder may be utilized to help retain the fibers in their rearranged locations, as is also well known by those skilled in the art. The fabric can be made of naturally occurring fibers, synthetic fibers, or blends thereof. Typical facing sheets made of a polyester type material can have weight of about 0.75 oz.-/yd.$^2$.

In addition, facing sheet 20 can be formed of a non-apertured material, such as a nonwoven isotropic web, or the like. In all of the aforementioned facing materials, the material should be relatively hydrophobic so as to retard wicking within the facing layer. Also suitable porous polymeric sheet materials such as polyalkylene webs having a fibrous surface, and the like.

Highly moisture-absorbent fibrous pad or batt 22, which usually is substantially rectangular in shape but smaller than the facing sheet and the backing sheet, can be formed in accordance with the teachings of U.S. Pat. No. 3,612,055 to Mesek et al. If desired, a highly moisture-absorbing layer can be provided substantially coextensive with backing sheet 24 and facing sheet 20.

A suitable backing sheet material for the diapers embodying the present invention can be an opaque polyethylene web about 0.001 thick. Another suitable material for this purpose is a polyethylene terephthalate web having a thickness of about 0.0005. Typical disposable diapers which can be fitted with tap-type adhesive fasteners described hereinabove are shown in U.S. Pat. No. 3,612,055 to Mesek et al. and in U.S. Pat. No. 3,683,916 to Mesek et al. Other suitable disposable diaper structures which can be improved by the present tab-type fasteners are shown in U.S. Pat. No. Re. 26,151 to Duncan et al.

In use, a diaper equipped with the adhesive fasteners of the present invention is applied to the infant by laying out the diaper on a suitable flat surface and placing the infant thereon so that the waist-underlying end of the diaper is that having the tab fastener means. The other end of the diaper then extends downwardly between the infant's legs. Next, the downwardly extending end of the diaper is brought up between the infant's leg to a position contiguous with the front of the infant's waist. The diaper is thereafter secured to the infant by placing the corners of the waist portion of the abdomen-covering end as far around the infant's waist as they will go and by bringing the corners of the underlying end of the diaper into an overlapping relationship with the aforementioned corners so that the diaper snugly encircles the infant's waist and provides a custom fit. The adhesive fasteners are then prepared for use by pulling free end 30 away from its temporary engagement with release means 52, exposing adhesive coating 50 which was releasably adhered to release means 52. The tabs are then used to secure the diaper in the desired position by simply urging the pressure-sensitive adhesive surfaces in contact with the adjacent outer surface of the diaper. The applied diaper assumes the configuration illustrated in FIG. 5.

The foregoing description and the drawing are illustrative but are not to be taken as limiting. Still other variations and modifications are possible without departing from the spirit and scope of the present invention.

I claim:
1. A disposable diaper having a facing sheet defining a diaper inside surface for direction toward an infant, a moisture-impervious backing sheet substantially coextensive with said facing sheet and defining a diaper outside surface, an absorbent panel positioned between said facing sheet and said backing sheet, and an adhesive tab fastener means which comprises:
 an integral elongated tape segment having a free working end which extends longitudinally to one transverse edge of said tape segment and a fixed end which extends longitudinally from said free working end to an opposite transverse edge of said tape segment, said fixed end having an adhesive coating on one face thereof for permanently attaching said tape segment to said backing sheet at a marginal location thereof, and including at least two substantially coplanar anchoring legs;
 a pressure-sensitive adhesive coating on one face of said free working end; and
 release means releasably attached to said adhesive coating on said free working end;
 said anchoring legs being contiguous at a location spaced from said transverse edge of said fixed end and diverging with respect to one another to a spaced-apart position at said transverse edge of said fixed end for facilitating distribution of stresses imposed on said tape segment; and
 said free end being separable from said release means to make said adhesive-coated free end of said tape segment available for use in securing said diaper about an infant.

2. The disposable diaper as defined in claim 1 wherein said tape segment is made of an elastic material.

3. The disposable diaper as defined in claim 1 wherein said fixed end is divided lengthwise to define anchoring legs which extend from the transverse edge of said fixed end to a location intermediate said transverse edges, and wherein said location is adjacent to a longitudinal margin of said diaper.

4. The disposable diaper as defined in claim 1 wherein said fixed end is divided lengthwise to define anchoring legs which extend from the transverse edge of said fixed end to a location intermediate said transverse edges, and wherein said location is spaced inwardly from a longitudinal margin of said diaper.

5. The disposable diaper as defined in claim 1 wherein said fixed end includes a middle anchoring leg and at least two anchoring legs flanking said middle leg, said flanking legs diverging from said middle leg in opposite directions.

6. The disposable diaper as defined in claim 1 wherein said adhesive coating on said fixed end is a pressuresensitive adhesive coating and wherein said adhesive coatings on said free end and said fixed end comprise a substantially continuous coating on one face of said tape segment.

7. The disposable diaper as defined in claim 1 wherein said release means is carried by said diaper at a marginal location thereon and provides a release region facing in the same direction as said diaper inside surface, wherein said free end is movable from a folded-over storage position, in which said free end is releasably adhered to said release region, to a working position in which said adhesive-coated free end of said tape segment is available for use in securing said diaper about an infant.

8. The disposable diaper as defined in claim 7 wherein said release means comprises a ribbon segment carried by said diaper and provided with a release coating substantially coextensive with said free end of said tape segment and facing in the same direction as said diaper inside surface.

9. The disposable diaper as defined in claim 7 wherein said release means is a release coating on a portion of said diaper inside surface.

10. The disposable diaper as defined in claim 9 wherein said release coating comprises a silicone release compound.

11. The disposable diaper as defined in claim 7 wherein a portion of said free end projects beyond the outermost edge of said adhesive coating carried by said free end, and wherein said projecting portion provides a gripping means for separating said tape segment from said release means when fastening said diaper about said infant.

12. The disposable diaper as defined in claim 1 wherein said fixed end comprises a pair of anchoring legs.

* * * * *